United States Patent
Markosyan et al.

(10) Patent No.: US 10,278,411 B2
(45) Date of Patent: *May 7, 2019

(54) HIGHLY SOLUBLE STEVIA SWEETENER

(71) Applicant: PureCircle Sdn Bhd, Kuala Lumpur (MY)

(72) Inventors: Avetik Markosyan, Yerevan (AM); Siddhartha Purkayastha, Chicago, IL (US); Marquita L. Johnson, Oak Lawn, IL (US); Monica Moralma Garces Ortega, Westmont, IL (US)

(73) Assignee: PureCircle Sdn Bhd, Kuala Lumpur (MY)

( * ) Notice: Subject to any disclaimer, the term of this patent is extended or adjusted under 35 U.S.C. 154(b) by 0 days.

This patent is subject to a terminal disclaimer.

(21) Appl. No.: 14/938,362

(22) Filed: Nov. 11, 2015

(65) Prior Publication Data

US 2016/0058051 A1    Mar. 3, 2016

Related U.S. Application Data

(63) Continuation of application No. 14/239,562, filed as application No. PCT/US2012/051163 on Aug. 16, 2012, now abandoned, which is a continuation-in-part of application No. PCT/US2012/024585, filed on Feb. 10, 2012, and a continuation-in-part of application No. PCT/US2012/043294, filed on Jun. 20, 2012.

(60) Provisional application No. 61/531,802, filed on Sep. 7, 2012.

(51) Int. Cl.
| | | |
|---|---|---|
| A23L 5/00 | (2016.01) | |
| A61K 47/26 | (2006.01) | |
| A23L 2/60 | (2006.01) | |
| A61K 8/60 | (2006.01) | |
| A61Q 19/00 | (2006.01) | |
| A23P 10/40 | (2016.01) | |
| A23L 29/00 | (2016.01) | |
| A23L 29/10 | (2016.01) | |
| A23L 29/20 | (2016.01) | |
| A23L 29/206 | (2016.01) | |
| A23L 29/219 | (2016.01) | |
| A23L 29/30 | (2016.01) | |
| A23L 27/00 | (2016.01) | |
| A23L 27/30 | (2016.01) | |
| A23L 5/40 | (2016.01) | |
| A23L 33/21 | (2016.01) | |

(52) U.S. Cl.
CPC ...... *A23L 5/00* (2016.08); *A23L 2/60* (2013.01); *A23L 5/40* (2016.08); *A23L 27/00* (2016.08); *A23L 27/30* (2016.08); *A23L 27/32* (2016.08); *A23L 27/36* (2016.08); *A23L 27/37* (2016.08); *A23L 27/82* (2016.08); *A23L 29/00* (2016.08); *A23L 29/035* (2016.08); *A23L 29/10* (2016.08); *A23L 29/20* (2016.08); *A23L 29/206* (2016.08); *A23L 29/219* (2016.08); *A23L 29/30* (2016.08); *A23L 29/35* (2016.08); *A23L 29/37* (2016.08); *A23L 33/21* (2016.08); *A23P 10/40* (2016.08); *A61K 8/602* (2013.01); *A61K 47/26* (2013.01); *A61Q 19/00* (2013.01); *A23V 2002/00* (2013.01); *A61K 2800/10* (2013.01); *A61K 2800/5922* (2013.01)

(58) Field of Classification Search
CPC .......... A23L 1/236; A23L 1/22; A23L 1/2363
See application file for complete search history.

(56) References Cited

U.S. PATENT DOCUMENTS

| | | | |
|---|---|---|---|
| 2008/0292764 A1† | 11/2008 | Prakash | |
| 2009/0004355 A1* | 1/2009 | Catani | A23L 1/2364 426/548 |
| 2011/0104353 A1† | 5/2011 | Lee | |
| 2011/0189360 A1† | 8/2011 | Yoo | |

FOREIGN PATENT DOCUMENTS

WO    2012082677 A1 †    6/2012

\* cited by examiner
† cited by third party

*Primary Examiner* — Katherine D Leblanc
(74) *Attorney, Agent, or Firm* — Briggs and Morgan, P.A.; Audrey J. Babcock

(57) ABSTRACT

A method for making highly soluble *Stevia* sweetener compositions is described. The resulting sweetener compositions readily provide high concentration solutions, and also possess superior taste qualities. The compositions can be used as sweeteners, sweetness enhancers, and flavor enhancers in foods, beverages, cosmetics and pharmaceuticals.

18 Claims, No Drawings

HIGHLY SOLUBLE STEVIA SWEETENER

FIELD OF THE INVENTION

The invention relates to a process for the preparation of highly soluble sweet glycosides from a *Stevia rebaudiana* Bertoni plant, and more particularly for preparation of highly soluble compositions containing rebaudioside D.

DESCRIPTION OF THE RELATED ART

The extract of *Stevia rebaudiana* plant (*Stevia*) contains a mixture of different sweet diterpene glycosides, which have a common aglycon-steviol and differ by the presence of carbohydrate residues at positions C13 and C19 of steviol molecule. These glycosides accumulate in *Stevia* leaves and compose approximately 10%-20% of the total dry weight. Typically, on a dry weight basis, the four major glycosides found in the leaves of *Stevia* are Dulcoside A (0.3%), Rebaudioside C (0.6-1.0%), Rebaudioside A (3.8%) and Stevioside (9.1%). Other glycosides identified in *Stevia* extract include Rebaudioside B, C, D, E, and F, Steviolbioside and Rubusoside. Steviol glycosides differ from each other by their taste properties. Some of them possess significant bitterness, lingering licorice aftertaste (Prakash I., DuBois G. E., Clos J. F., Wilkens K. L., Fosdick L. E. (2008) *Development of rebiana, a natural, non-caloric sweetener, Food Chem. Toxicol.*, 46, S75-S82).

REBAUDIOSIDE D

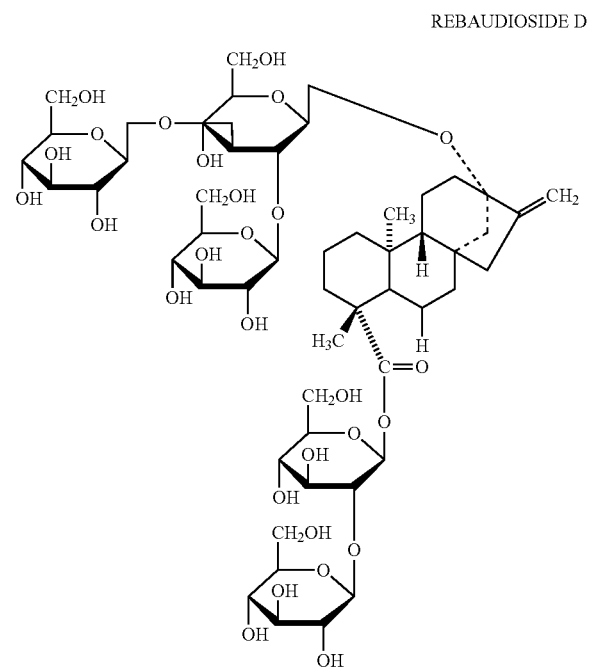

Rebaudioside D or Reb D (CAS No: 63279-13-0), is one of the sweet glycosides found in *Stevia rebaudiana*. Studies show that Reb D possess very desirable taste profile, almost lacking bitterness, and lingering licorice aftertaste typical for other Steviol glycosides.

These properties multiply the significance of Reb D and attract great interest for methods of preparation of Reb D.

However highly purified steviol glycosides possess relatively low water solubility. For example Rebaudioside A (Reb A) thermodynamic equilibrium solubility at room temperature is only 0.8%.

On the other hand, it is well known that steviol glycosides exhibit so-called polymorphism (Zell T. M., Padden B. E., Grant D. J. W., Schroeder S. A., Wachholder K. L., Prakash I., Munsona E. J. (2000) *Investigation of Polymorphism in Aspartame and Neotame Using Solid-State NMR Spectroscopy, Tetrahedron*, 56, 6603-6616). Particularly Reb A amorphous, anhydrous and solvate forms differ significantly from each other in terms of solubility which is one of the main criteria for the commercial viability of a sweetener. In this regard, as shown in Table 1, the hydrate form of Reb A displays the lowest solubility (Prakash I., DuBois G. E., Clos J. F., Wilkens K. L., Fosdick L. E. (2008) *Development of rebiana, a natural, non-caloric sweetener, Food Chem. Toxicol.*, 46, S75-S82). It was shown that Reb A may transform from one polymorph form to another at certain conditions (U.S. patent application Ser. No. 11/556,049).

TABLE 1

Properties of Rebaudioside A forms (U.S. patent application Ser. No. 11/556,049)

| | Polymorph Forms | | | |
|---|---|---|---|---|
| | Form 1 Hydrate | Form 2 Anhydrous | Form 3 Solvate | Form 4 Amorphous |
| Rate of dissolution in $H_2O$ at 25° C. | Very low (<0.2% in 60 minutes) | Intermediate (<30% in 5 minutes) | High (>30% in 5 minutes) | High (>35% in 5 minutes) |
| Alcohol content | <0.5% | <1% | 1-3% | <0.05% |
| Moisture content | >5% | <1% | <3% | 6.74% |

Reb D possesses even lower water solubility compared to Reb A. At room temperature it can be dissolved only at 0.01-0.05%. When heat is applied one can make up to 0.5% solution. However, upon cooling to room temperature, Reb D will quickly crystallize back from solution. Considering high sweetness intensity of Reb D (about 200 times of sugar sweetness)—even 0.05% solubility may seem sufficient for many applications.

Many food production processes use highly concentrated ingredient mixes prior to producing final forms of food products. In that case, much higher concentrations of dissolved Reb D will be required. It is noted that using heat for dissolution of Reb D may not be possible in compositions containing heat sensitive components. Also maintaining high temperature of mixture for prolonged time to prevent premature crystallization of Reb D can cause thermal degradation of mixture components or undesirable changes of organoleptic properties.

U.S. patent application Ser. No. 12/612,374 describes a preparation method of anhydrous form of Reb D which possesses about 0.15% solubility at 50° C. The method requires heat treatment of Reb D powder at a temperature 80°-110° C. for about 50-120 hours, under vacuum. It is noted that the described method allows preparing Reb D form that has limited solubility and still requires significant increase of temperature for dissolution. Extended time period of said vacuum thermal treatment is a disadvantage as well.

U.S. patent application Ser. No. 12/700,223 describes method of preparing supersaturated solutions of Reb D, wherein the mixture of Reb D with aqueous liquid is heated to 75°-90° C. and then gradually cooled to provide relatively stable 0.3% Reb D solution. It is noted that the said method describes only a solubilization technique for a specific aqueous liquid, and does not provide readily usable form of highly soluble Reb D.

U.S. patent application Ser. No. 13/022,727 describes inclusion complexes of steviol glycosides and cyclodextrins, wherein glycoside to cyclodextrin ratio ranges from 1:1 to 1:20 and the solubility of said complexes range from 0.1-7%. It is noted that some techniques described within the application, such as freeze-drying, are difficult to implement in large-scale multi-ton productions. The significant portion on non-sweet (low sweetness) compound, (i.e. cyclodextrin), reduces the overall sweetness of the mixture as well.

There is a need for developing highly soluble forms or compositions of Reb D that possess high sweetness intensity, and provide stable solutions at room temperature.

Furthermore, considering the similar chemical structures of Reb D and other steviol glycosides, as well as other terpene glycosides, there is also a need to develop approaches that may be used in case of other glycosides as well.

SUMMARY OF THE INVENTION

The invention is directed to a method for producing a sweetener comprising the steps of providing *Stevia* sweetener powder, solubilizing it in water under gradient temperature treatment conditions, to produce highly stable concentrated solution, and spray drying the highly stable concentrated solution to obtain a highly soluble *Stevia* sweetener powder.

Hereinafter the term "steviol glycoside(s)" will mean Rebaudioside A, Rebaudioside B, Rebaudioside C, Rebaudioside D, Rebaudioside E, Rebaudioside F, Stevioside, Steviolbioside, Dulcoside A, Rubusoside, or other glycoside of steviol and combinations thereof.

Hereinafter, unless specified otherwise the solubility of material is determined in reverse osmosis (RO) water at room temperature. Where the solubility is expressed as "%" it to be understood as number of grams of material soluble in 100 grams of solvent.

It is to be understood that both the foregoing general description and the following detailed description are exemplary and explanatory and are intended to provide further explanation of the invention as claimed.

DETAILED DESCRIPTION OF THE INVENTION

A process for the preparation of highly soluble *Stevia* sweetener, particularly a *Stevia* sweetener comprising Reb D, is described herein.

Crystalline Reb D has an inherently low solubility, ranging from about 0.01%-0.05%. The need exists, therefore, for a process in which a high solubility Reb D or compositions thereof are prepared.

In one embodiment of the present invention, initial materials, comprising sweet glycoside(s) of the *Stevia rebaudiana* Bertoni plant extract, which includes Rebaudioside D, Stevioside, Rebaudioside A, Rebaudioside B, Rebaudioside C, Rebaudioside E, Rebaudioside F, Steviolbioside, Dulcoside A, Rubusoside or other glycoside of steviol and combinations thereof were combined with the water at ratio of 1:1 to 1:10, preferably 1:3 to 1:6 (w/v).

The obtained mixture was further subjected to a gradient heat treatment that resulted in high stability and high concentration solution. The gradient of 1° C. per minute was used in heating the mixture. The mixture was heated to the temperature of 110-140° C., preferably 118-125° C. and was held at maximum temperature for 0-120 min, preferably 50-70 min.

After the heat treatment the solution was cooled down to about 80° C. at gradient of 1° C. per minute. This high stability and high concentration solution did not show any crystallization during up to 1-hour incubation.

The solution was spray dried by laboratory spray drier operating at 175° C. inlet and 100° C. outlet temperature. A highly soluble amorphous compositions of Reb D were obtained with >1% solubility in water at room temperature.

In another embodiment of this invention the initial materials were selected from the group including Reb D, Reb A, Rebaudioside B (Reb B), and steviolbioside (Sbio)

In yet another embodiment combining the Reb D and Reb B, treating and spray drying it by the methods described above, yields a composition with significantly higher solubility (about 1%) compared to the composition obtained by combination of Reb D and Reb A at the same ratio (about 0.5%). This phenomenon was unexpected, as both Reb D and Reb B have <0.1% solubility, whereas the Reb A used in the experiment had >5% solubility. Therefore combinations of Reb D and Reb A were expected to have higher solubility compared to combinations of Reb D and Reb B.

In one embodiment the said combination comprises Reb D and Reb B at a ratio from 50%:50% to 80%:20%, preferably 70%:30% to 80%:20%. The resulting product has a solubility ranging from 0.5% to 2%.

In yet another embodiment the Reb B was fully or partially, converted into carboxylate salt form. The solution containing RebD and Reb B, after heat treatment and subsequent cooling (as described above), was mixed with solution of base to achieve a pH level of 4.5-7.0, preferably pH 5.5-6.5. The obtained mixture was spray dried as described above. Alternatively other reactions able to convert Reb B into carboxylate salt form may be used as well. The preferred cations were $K^+$ and $Na^+$, and the bases—KOH and NaOH respectively. However those skilled in art should recognize that other carboxylate salts of Reb B can be prepared in a similar manner.

In one embodiment the taste properties of compositions comprising Reb D and Reb B were compared with compositions comprising Reb D and Reb A at the same ratio. The evaluation shows that combinations of Reb D and Reb B possessed superior taste properties compared to combinations of Reb D and Reb A. Particularly the compositions of Reb D and Reb B showed almost no lingering and bitterness, and more rounded sugar-like taste profile.

The obtained compositions can be used as sweetener, sweetness enhancer, and flavor enhancer in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the compositions can be used in drug or pharmaceutical preparations and cosmetics, including but not limited to toothpaste, mouthwash, cough syrup, chewable tablets, lozenges, vitamin preparations, and the like.

The compositions can be used "as-is" or in combination with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, dulcoside A, steviolbioside, rubusoside, as well as other steviol glycosides found in Stevia rebaudiana Bertoni plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include lemon, orange, fruit, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilizers, thickeners, gelling agents.

The following examples illustrate preferred embodiments of the invention. It will be understood that the invention is not limited to the materials, proportions, conditions and procedures set forth in the examples, which are only illustrative.

EXAMPLE 1

Preparation of Reb D Concentrated Solution 100 g of rebaudioside D produced by PureCircle Sdn Bhd (Malaysia), with 98.1% purity (dry weight basis), having water solubility of 0.03% at room temperature was mixed with 400 g of water and incubated in thermostatted oil bath. The temperature was increased at 1° C. per minute to 121° C. The mixture was maintained at 121° C. for 1 hour and then the temperature was decreased to 80° C., at 1° C. per minute to make Solution#1.

EXAMPLE 2

Preparation of Reb D and Reb A Concentrated Solution 70 g of rebaudioside D with 98.1% purity (dry weight basis), having water solubility of 0.03% and 30 g of rebaudioside A with 98.6% purity (dry weight basis), and having water solubility of 5.5%, both produced by PureCircle Sdn Bhd (Malaysia), were mixed with 400 g water and subjected to heat treatment as described in EXAMPLE 1 to make Solution#2.

EXAMPLE 3

Preparation of Reb D and Reb B Concentrated Solution 70 g of rebaudioside D with 98.1% purity (dry weight basis), having water solubility of 0.03% and 30 g of rebaudioside B with 99.0% purity (dry weight basis), and having water solubility of 0.01%, both produced by PureCircle Sdn Bhd (Malaysia), were mixed with 400 g water and subjected to heat treatment as described in EXAMPLE 1 to make Solution#3.

EXAMPLE 4

Concentrated Solution Stability

Solution#1, solution#2 and solution#3 prepared according to EXAMPLE 1, EXAMPLE 2 and EXAMPLE 3 were assessed in terms of their stability. The results are summarized in Table 2.

TABLE 2

Concentrated solution stability (80° C.)

| Time, min | Observation | | |
|---|---|---|---|
| | Solution#1 | Solution#2 | Solution#3 |
| 1 | Cloudy solution | Clear solution | Clear solution |
| 5 | Intensive crystallization | Cloudy solution | Clear solution |
| 15 | Viscous slurry of crystals | Intensive crystallization | Clear solution |
| 30 | Solidified crystalline mixture | Viscous slurry of crystals | Clear solution |
| 60 | Solidified crystalline mixture | Solidified crystalline mixture | Cloudy solution |

It can be seen that the solution prepared by combining reb D and reb B shows greater stability towards crystallization.

EXAMPLE 5

Preparation of Highly Soluble Rebaudioside D Compositions

Freshly prepared solution#1, solution#2 and solution#3 prepared according to EXAMPLE 1, EXAMPLE 2 and EXAMPLE 3 were spray dried using YC-015 laboratory spray drier (Shanghai Pilotech Instrument & Equipment Co. Ltd., China) operating at 175° C. inlet and 100° C. outlet temperature. Solutions were maintained at 80° C. to prevent premature crystallization. The solution#1 yielded sample #1, solution #2 yielded sample #2 and solution #3 yielded sample #3.

The obtained amorphous powder samples were compared for solubility (Table 3).

TABLE 3

Solubility of Rebaudioside D compositions

| Solubility, % | Observation | | |
|---|---|---|---|
| | Sample#1 | Sample#2 | Sample#3 |
| 0.01 | Clear solution | Clear solution | Clear solution |
| 0.05 | Slightly cloudy solution | Clear solution | Clear solution |
| 0.5 | Cloudy solution | Slightly cloudy solution | Clear solution |
| 1.0 | Visible undissolved matter | Cloudy solution | Clear solution |
| 1.5 | Visible undissolved matter | Visible undissolved matter | Slightly cloudy solution |

EXAMPLE 6

Taste Profile of Rebaudioside D Compositions

Taste profiles of sample#1, sample#2 and sample#3 prepared according to EXAMPLE 5 were compared. A model zero-calorie carbonated beverage according to formula presented below was prepared.

| Ingredients | Quantity, % |
|---|---|
| Cola flavor | 0.340 |
| ortho-Phosphoric acid | 0.100 |
| Sodium citrate | 0.310 |
| Sodium benzoate | 0.018 |
| Citric acid | 0.018 |
| Sample# 1 or 2 or 3 | 0.050 |
| Carbonated water | to 100 |

The sensory properties were evaluated by 20 panelists. The results are summarized in Table 4.

TABLE 4

Evaluation of zero-calorie carbonated beverage samples

| Taste attribute | Number of panelists detected the attribute | | |
|---|---|---|---|
| | Sample #1 | Sample #2 | Sample #3 |
| Bitter taste | 0 | 10 | 0 |
| Astringent taste | 0 | 12 | 1 |
| Aftertaste | 0 | 11 | 1 |
| Comments | | | |
| Quality of sweet taste | Clean (20 of 20) | Bitter aftertaste (11 of 20) | Clean (18 of 20) |
| Overall evaluation | Satisfactory (20 of 20) | Satisfactory (7 of 20) | Satisfactory (17 of 20) |

The above results show that the beverages prepared using the compositions comprising Reb D and Reb B (sample#3) possessed almost similar taste, profile with pure reb D (sample #1), at the same time exceeding pure Reb D in solubility almost 20 times. On the other hand compositions comprising Reb D and Reb A (sample#2) possessed inferior solubility and taste profile compared to sample #3.

EXAMPLE 7

Preparation of Reb D and Reb B Carboxylate Salt Composition 70 g of rebaudioside D with 98.1% purity (dry weight basis), having water solubility of 0.03% and 30 g of rebaudioside B with 99.0% purity (dry weight basis), and having water solubility of 0.01%, both produced by PureCircle Sdn Bhd (Malaysia), were mixed with 400 g water and subjected to heat treatment as described in EXAMPLE 1 to make concentrated solution. The pH of the solution was adjusted with 40% KOH to pH 6.0 and the solution was spray dried as described in EXAMPLE 5. The taste profile of obtained carboxylate salt composition was compared with sample#3 of EXAMPLE 5, according to procedure described in EXAMPLE 6. No significant differences between sample #3 and the carboxylate salt composition were revealed during the comparison.

The process of the present invention resulted in a Rebaudioside D compositions that demonstrated high degree of solubility in water, and superior taste profile. Although the foregoing embodiments describe the use of Rebaudioside D, Rebaudioside B and Rebaudioside A, it is to be understood that any Stevia-based sweetener may be used and prepared in accordance with this invention, and all Stevia-based sweeteners are contemplated to be within the scope of the present invention.

Although the invention and its advantages have been described in detail, it should be understood that various changes, substitutions and alterations can be made herein without departing from the spirit and scope of the invention as defined by the appended claims. Moreover, the scope of the application is not intended to be limited to the particular embodiments of the invention described in the specification. As one of ordinary skill in the art will readily appreciate from the disclosure of the invention, the compositions, processes, methods, and steps, presently existing or later to be developed that perform substantially the same function or achieve substantially the same result as the corresponding embodiments described herein may be utilized according to the invention.

We claim:

1. A method for producing a high solubility *Stevia* sweetener comprising the steps of:
   A) providing Rebaudioside D as a first *Stevia* sweetener;
   B) providing Rebaudioside B as a second *Stevia* sweetener;
   C) providing water;
   D) mixing the water and first and second *Stevia* sweeteners to make a mixture;
   E) increasing the temperature of the mixture by a gradient heat treatment method having a rate of temperature change of about 1° C. per minute to make a solution;
   F) holding the solution at an elevated temperature; and
   G) decreasing the temperature of the solution at a constant rate by a gradient cooling method to obtain a high stability and high concentration *Stevia* sweetener solution;
   wherein the high solubility *Stevia* sweetener has a solubility of 0.5-2 grams per 100 grams of water at room temperature.

2. The method of claim 1 wherein a ratio of the first and second *Stevia* sweeteners is about 99:1 to 1:99 (w/w).

3. The method of claim 1 wherein a ratio of water to the combined first and second *Stevia* sweeteners is about 1:1 to 10:1 (v/w).

4. The method of claim 1 wherein the water and *Stevia* sweetener mixture is heated to a temperature of about 118-125° C.

5. The method of claim 1 wherein the water and *Stevia* sweetener mixture is held at a temperature of about 118-125° C. for a period of about 50-70 minutes.

6. The method of claim 1 wherein the temperature of the solution is cooled down to a temperature of about 80° C. at gradient of about 1° C. per minute to obtain the high stability and high concentration *Stevia* sweetener solution.

7. The method of claim 1 wherein high stability and high concentration *Stevia* sweetener solution is spray dried to provide the high solubility *Stevia* sweetener.

8. The method of claim 1, wherein a pH of high stability and high concentration *Stevia* sweetener solution is adjusted by alkaline solution to about pH 4.5 to 7.0.

9. A high solubility *Stevia* sweetener made by the process of claim 1, having a solubility of 0.5-2 grams per 100 grams of water at room temperature.

10. A high solubility *Stevia* sweetener made by the process of claim 1, comprising a mixture of rebaudioside D and rebaudioside B, wherein rebaudioside B, is partially or fully converted to a carboxylate salt.

11. A sweetener composition comprising a high solubility *Stevia* sweetener made by the process of claim 1 and an additional sweetening agent selected from the group consisting of: stevia extract, steviol glycosides, stevioside, rebaudioside A, rebaudioside B, rebaudioside C, rebaudioside D, rebaudioside E, rebaudioside F, dulcoside A, steviolbioside, rubusoside, other steviol glycosides found in *Stevia rebaudiana* Bertoni plant and mixtures thereof, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols, and a combination thereof.

12. A flavor composition comprising a high solubility *Stevia* sweetener made by the process of claim 1 and an additional flavoring agent selected from the group consisting of: lemon, orange, fruit, banana, grape, pear, pineapple, mango, bitter almond, cola, cinnamon, sugar, cotton candy, vanilla, and a combination thereof.

13. A food ingredient comprising a high solubility *Stevia* sweetener made by the process of claim 1 and an additional food ingredient selected from the group consisting of: acidulants, organic and amino acids, coloring agents, bulking agents, modified starches, gums, texturizers, preservatives, antioxidants, emulsifiers, stabilizers, thickeners, gelling agents, and a combination thereof.

14. A food, beverage, cosmetic or pharmaceutical product comprising high solubility *Stevia* sweetener made by the process of claim 1.

15. The method of claim 1, wherein the ratio of the first and second *Stevia* sweeteners is about 50:50 to 95:5 (w/w).

16. The method of claim 1, wherein the ratio of the first and second *Stevia* sweeteners is about 70:30 to 90:10 (w/w).

17. The method of claim 1, wherein a ratio of water to the combined first and second *Stevia* sweeteners is about 3:1 to 6:1 (v/w).

18. The method of claim 1, wherein a pH of high stability and high concentration *Stevia* sweetener solution is adjusted by alkaline solution to about pH 5.5 to 6.0.

\* \* \* \* \*